US00PP32443P2

(12) United States Plant Patent
Häusler et al.

(10) Patent No.: US PP32,443 P2
(45) Date of Patent: Nov. 10, 2020

(54) ***MUEHLENBECKIA* PLANT NAMED 'GOLDEN GIRL'**

(50) Latin Name: *Muehlenbeckia complexa*
Varietal Denomination: Golden Girl

(71) Applicants: Dirk Häusler, Isselburg (DE); Frank Häusler, Isselburg (DE)

(72) Inventors: Dirk Häusler, Isselburg (DE); Frank Häusler, Isselburg (DE)

( * ) Notice: Subject to any disclaimer, the term of this patent is extended or adjusted under 35 U.S.C. 154(b) by 0 days.

(21) Appl. No.: 16/602,918

(22) Filed: Dec. 24, 2019

(30) Foreign Application Priority Data

Oct. 21, 2019 (QZ) ..... PBR 20192676

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 6/30; A01H 5/02; A01H 6/00
See application file for complete search history.

*Primary Examiner* — Keith O. Robinson
(74) *Attorney, Agent, or Firm* — Penny J. Aguirre

(57) ABSTRACT

A new cultivar of hybrid *Muehlenbeckia* plant named 'Golden Girl' that is characterized by its short plant height and a compact plant habit, its young foliage that is yellow in color, and its mature foliage that is yellow-green in color.

2 Drawing Sheets

Botanical classification: *Muehlenbeckia complexa.*
Variety denomination: 'Golden Girl'.

BACKGROUND OF THE INVENTION

The present invention relates to a new and distinct cultivar of *Muehlenbeckia complexa* and will be referred to hereafter by its cultivar name, 'Golden Girl'. 'Golden Girl' represents a new herbaceous shrub grown for landscape use.

The Inventors discovered the new cultivar in May of 2018 as a naturally occurring branch mutation of *Muehlenbeckia* 'Maori' (not patented) that was growing in a container in a production block in Isselburg, Germany.

Asexual propagation of the new cultivar was first accomplished by softwood cuttings in June of 2018 under the direction of the Inventors in Isselburg, Germany. Asexual propagation by softwood stem cuttings has determined that the characteristics of this cultivar are be stable and are reproduced true to type in successive generations.

SUMMARY OF THE INVENTION

The following traits have been repeatedly observed and represent the characteristics of the new cultivar. These attributes in combination distinguish 'Golden Girl' as a unique cultivar of *Muehlenbeckia.*

1. 'Golden Girl' exhibits a short plant height and a compact plant habit.
2. 'Golden Girl' exhibits young foliage that is yellow in color.
3. 'Golden Girl' exhibits mature foliage that is yellow-green in color.

The parent plant, 'Maori', differs from 'Golden Girl' in having a less compact plant habit, young leaves that are green in color and mature leaves that are dark green in color. The new cultivar can also be compared to the *Muehlenbeckia complexa* cultivar 'Big Leaf' (not patented). 'Big Leaf' differs from 'Golden Girl' in having leaves that are larger in size and green in color.

BRIEF DESCRIPTION OF THE DRAWINGS

The plants in the accompanying photographs depict the characteristics of a two-year-old plant of 'Golden Girl' as grown outdoors in a 10-cm container in Isselburg, Germany.

The photograph in FIG. 1 provides a side view of the plant in bloom.

Figure 1:
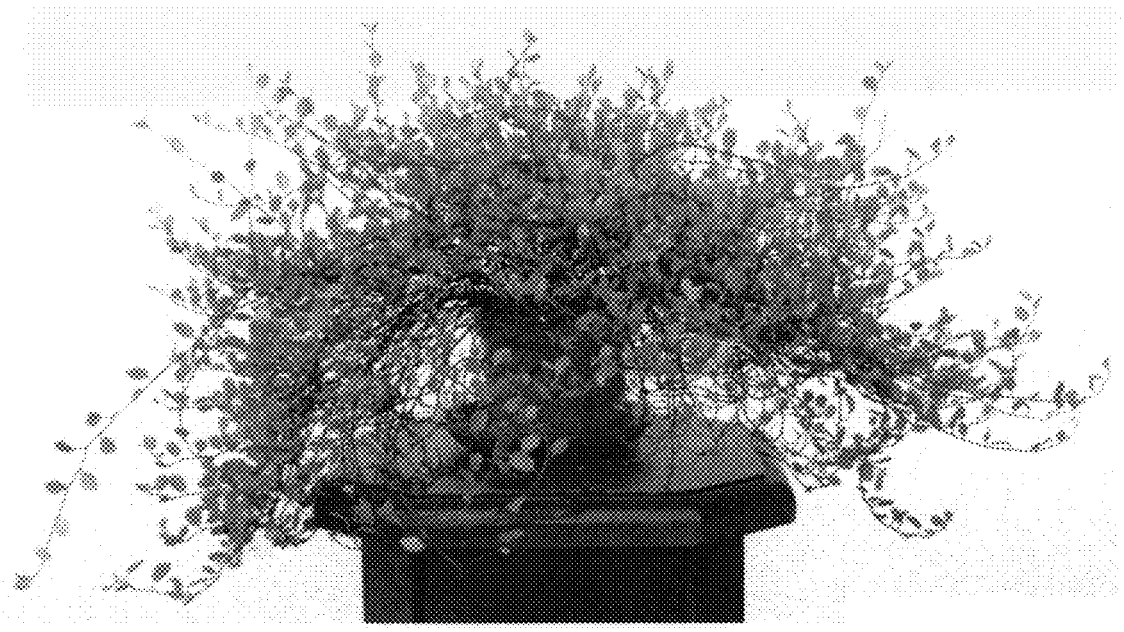
Figure 2:
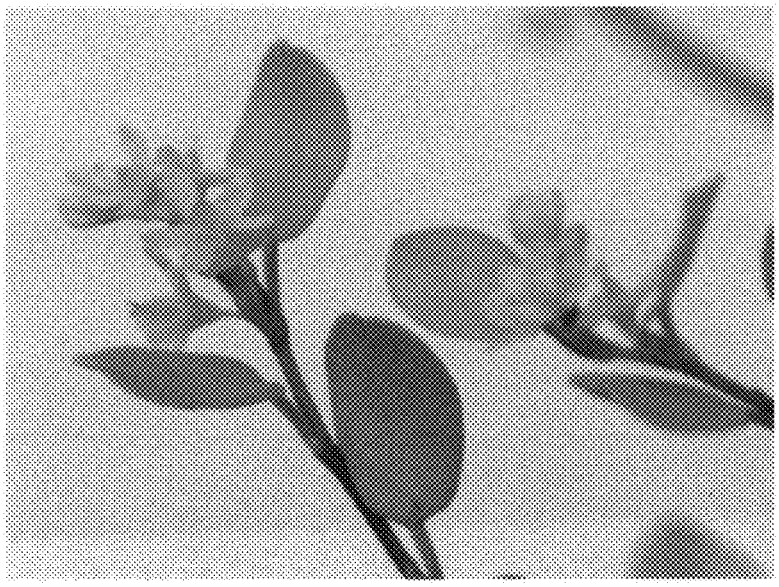

The photograph in FIG. 2 provides a close-up view of inflorescences of 'Golden Girl'.

Figure 3:
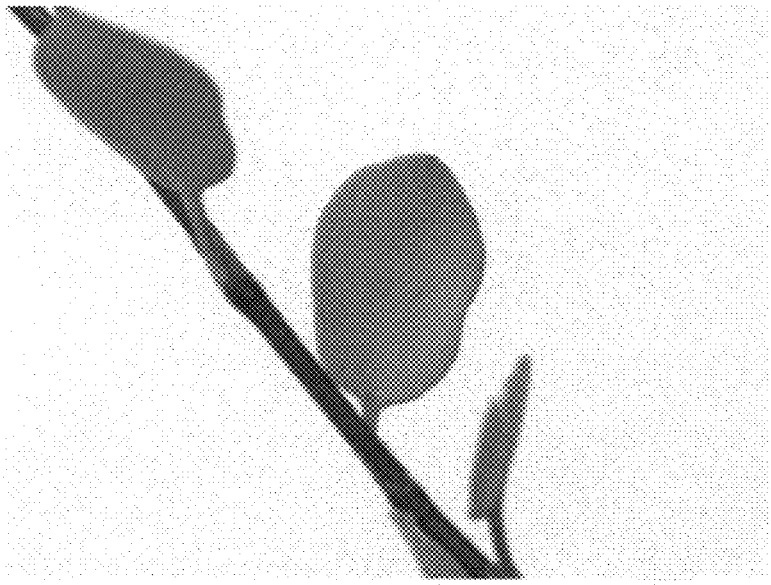

The photograph in FIG. 3 provides a close-up view of the foliage of 'Golden Girl'.

The colors in the photograph may differ slightly from the color values cited in the detailed botanical description, which accurately describe the colors of the new *Muehlenbeckia.*

BOTANICAL DESCRIPTION OF THE PLANT

The following is a detailed description of two-year-old plants of the new cultivar as grown outdoors in 10-cm containers in Isselburg, Germany. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to mid-summer in Germany.

*Plant type.*—Herbaceous shrub.

*Plant habit.*—Creeping to broadly spreading.

*Height and spread.*—Average of 19.8 cm from soil level to top of foliar plane, 12.4 cm from soil level to top of floral plane and 55.3 cm in spread as grown in a 10-cm container, 25 cm in height and 75 cm in spread as a mature plant in the landscape.

*Hardiness.*—At least in U.S.D.A. Zones 8 to 11.

*Diseases and pests.*—No Susceptibility or resistance to diseases or pests has been observed.

*Root description.*—Fibrous.

*Propagation.*—Stem cuttings.

*Root development.*—An average of 40 days for root initiation with a finished (saleable) plant produced in about 9 months.

*Growth rate.*—Moderately vigorous.

Stem description:

*Branch shape.*—Rounded.

*Branch color.*—Young stems; 171A to 171B, mature stems 183A, older stems and bark 200A.

*Branch size.*—Average of 1.2 mm in diameter and an average of 24.5 cm in length.

*Branch surface.*—Matte and densely covered with very small glands; average of 0.1 mm in diameter, and too small to measure color, at the base there is a single ochrea membranous sheath around the stem; an average of 2 mm in length and 199B to 199C.

*Branch strength.*—Strong.

*Branch aspect.*—Stems grow in a zig-zag distichous leaf arrangement.

*Branching.*—Very freely branching, average of 25 primary branches and 10 lateral branches per primary stem.

Foliage description:

*Leaf shape.*—Obovate to broadly obovate.

*Leaf division.*—Simple.

*Leaf base.*—Obtuse to straight.

*Leaf apex.*—Broadly acute.

*Leaf venation.*—Pinnate, upper surface; 152D, lower surface; 146C.

*Leaf margins.*—Entire.

*Leaf attachment.*—Petiolate.

*Leaf arrangement.*—Alternate, distichous.

*Internode length.*—An average of 1.2 cm.

*Leaf size.*—Average of 1.3 cm in length and 9 mm in width.

*Leaf color.*—Young upper and lower surface color 151A, narrowly margined N170B, mature upper and lower surface color 144A.

*Leaf surface.*—Both surfaces are smooth, glabrous, non-rugose and slightly glossy.

*Petioles.*—Average of 5 mm in length, 7.5 mm in diameter, strong, color; upper surface 199A, lower surface 199A to 199B and tinged 182B at the proximal end, both surfaces smooth and densely covered with very small glands; an average of 0.1 mm and too small to measure color.

Flower description:

*Type.*—Axillary and terminal racemes.

*Lastingness of inflorescence.*—Average of 10 days.

*Inflorescence size.*—An average of 1.2 cm in height and 7 mm in diameter.

*Flower quantity.*—Average of 9 per inflorescence and 300 per plant.

*Flower type.*—Rotate, single, self-cleaning.

*Flower aspect.*—Upright to outward.

*Flower size.*—Average of 4.5 mm in diameter and 3 mm in depth.

*Fragrance.*—None.

*Buds.*—Ovate in shape, average of 1.25 cm in diameter and 2 mm in length, surface is smooth, glabrous and matte, between 150C and 150D in color.

*Petals.*—No separate petals or sepals present.

*Tepals.*—Rotate, average of 5, whorled in a single row, broadly oblong in shape, average of 2 mm in length and 1.2 mm in width, obtuse apex, fused base, entire margin, upper and lower surface smooth, glabrous and slightly glossy, color; when opening upper surface 145C with center 145B, when opening lower surface 145C with center 145B and base 152C, fully open upper and lower surface 145C with center 145B.

*Peduncles.*—Average of 1 cm in length, 5 mm in diameter, held straight on top of lateral branch, strong, 199C in color and tinged with 177D, surface is matte, smooth, densely covered with very small glands average of 1 mm in diameter and too small to measure color, and glabrous except for single ochreas (membranous sheath) folded around the peduncle; an average of 2 mm in length, 199B to 199C in color.

*Pedicels.*—Average of 2 mm in length, 0.2 mm in diameter, held in a 30° angle to peduncle, strong, matte, smooth and glabrous surface, 145D in color.

Reproductive organs:

*Gynoecium.*—Pistil; 1, average of 2 mm in length, stigma; 3-parted, 5 mm in length, 0.75 mm in diameter, 157A, style; 1.5 mm in length and N144D in color, ovary; 145A in color.

*Androecium.*—Stamens; 9, filament; no filaments present, anthers sessile, anther; basifixed, triangular in shape, 2 mm in length and width and 150D in color, pollen; low in quantity and lighter than 150D in color.

*Fruit/seed.*—No fruit or seed detected to date.

It is claimed:

1. A new and distinct cultivar of *Muehlenbeckia* plant named 'Golden Girl' substantially as herein illustrated and described.

* * * * *